(12) United States Patent
Samuel et al.

(10) Patent No.: US 8,075,521 B2
(45) Date of Patent: Dec. 13, 2011

(54) CATHETER

(75) Inventors: Peter Samuel, Sunderland (GB); Christopher Hartley, Sunderland (GB)

(73) Assignee: City Hospitals Sunderland NHS Trust, Sunderland, Tyne and Wear (GB)

( * ) Notice: Subject to any disclaimer, the term of this patent is extended or adjusted under 35 U.S.C. 154(b) by 287 days.

(21) Appl. No.: 12/227,196

(22) PCT Filed: May 15, 2007

(86) PCT No.: PCT/GB2007/050267
§ 371 (c)(1), (2), (4) Date: Jan. 23, 2009

(87) PCT Pub. No.: WO2007/135458
PCT Pub. Date: Nov. 29, 2007

(65) Prior Publication Data
US 2009/0171280 A1  Jul. 2, 2009

(30) Foreign Application Priority Data

May 18, 2006 (GB) .................................. 0609854.5
Jul. 11, 2006 (GB) .................................. 0613742.6

(51) Int. Cl.
*A61M 29/00* (2006.01)
(52) U.S. Cl. ............ 604/97.01; 604/101.01; 604/103.03
(58) Field of Classification Search ............... 604/99.04, 604/97.01, 98.01, 101.01, 101.05, 103.03, 604/284; 128/202.15, 207.15, 207.29; 606/213, 606/215; 623/9
See application file for complete search history.

(56) References Cited

U.S. PATENT DOCUMENTS

| 5,772,639 A | 6/1998 | Lampropoulos et al. |
| 2007/0017527 A1* | 1/2007 | Totz .................. 128/207.15 |

FOREIGN PATENT DOCUMENTS

EP  0400369 A2  12/1990

* cited by examiner

*Primary Examiner* — Nicholas D Lucchesi
*Assistant Examiner* — Melissa A Snyder
(74) *Attorney, Agent, or Firm* — Thomas E. Sisson (57) ABSTRACT

A tracheo-oesophageal fistula catheter (1) comprises an elongate conduit (2) having a proximal and a distal end, the conduit (2) comprising a plurality of lumens commencing adjacent to the proximal end; means (8, 9) for substantially sealing a tracheo-oesophageal fistula, the means being attached to the conduit (2) adjacent to the proximal end and comprising two elements (8, 9) to be placed on either side of the fistula; and at least one expandable balloon (7) attached to the conduit (2) adjacent to the distal end, and in fluid connection with at least one of said lumens; wherein at least one lumen is a gastric lumen, the gastric lumen extending along the full length of the conduit and having an outlet (6) at the distal end of the conduit (2), and wherein at least one element of the means for sealing the fistula comprises an expandable balloon in fluid connection with at least one of said lumens.

9 Claims, 7 Drawing Sheets

CATHETER

FIELD OF THE INVENTION

The invention relates to catheters; in particular to catheters used to seal a tracheo-oesophageal fistula.

BACKGROUND OF THE INVENTION

A laryngectomy is a surgical procedure which involves the removal of a patient's voice box and other surrounding structures, usually for treatment of cancer of the larynx. During the procedure a permanent opening known as a tracheostoma or stoma is created in the patient's neck to allow air intake into the lungs through this opening, rather than through the mouth.

As the patient's voice box has been removed, most patients subsequently undergo a tracheo-oesophageal puncture in order to restore their speech. This involves the creation of a hole (a fistula) between the oesophagus and the trachea. This allows a one-way valve prosthesis to be fitted into this gap. Such valves enable air to pass one way from the lungs/trachea up through the oesophagus. Simultaneously this valve seals the gap in the opposition direction, and prevents leakage of food or saliva from the oesophagus through the trachea to the lungs, a potential source of chest infection.

The valve blocks the flow of secretions and food materials from the oesophagus to the airway, but allows a passage of air from the airway into the throat to permit speech.

Following tracheo-oesophageal puncture surgery, there may be periods of time during which the valve prosthesis is not in place, for example before the new valve is fitted. Alternatively a leaking valve may have to be removed and the fistula tissues 'rested' before a new valve can be fitted. When the valve is not in place the fistula must be sealed to prevent leakage of secretions and food materials into the airway which could cause infections. Typically this is done using a Foley's catheter, which is placed through the wound at the front of the neck, through the fistula and down the oesophagus into the stomach. The catheter is also used for feeding the patient.

The Foley's catheter was designed as a urethral catheter to provide continuous urinary drainage from the bladder. A balloon at one end of the catheter is inflated to retain the tip of the catheter in the bladder. When used to seal a tracheo-oesophageal fistula, the end of the Foley's catheter sits in the stomach and the balloon is inflated to prevent the tube moving out the stomach.

Using a Foley's catheter to seal the fistula relies on the tissues surrounding the fistula resting against the surface of the catheter to provide a seal between the oesophagus and trachea. This sometimes works adequately, but not always. The seal provided is sometimes not good enough to allow oral feeding, and when the valve is not in place the patient must be fed through the catheter directly into the stomach. If the seal is not adequate then there is an increased chance of infections as secretions from the oesophagus can leak into the trachea. A foleys catheter is not designed to be used in this way and can be uncomfortable for the patient to wear.

U.S. Pat. No. 4,836,204 describes a method for effecting closure of a perforation in the septum of the heart using a double-balloon catheter. The catheter is designed to be inserted through a vein, into the heart, and through the perforation. Once in place the balloons are inflated either side of the perforation to seal the gap. The other end of the catheter is buried in the patient's subcutaneous tissues and the catheter remains in position until open heart surgery can be carried out to correct the problem.

It would be desirable to provide an improved catheter specifically designed for use in sealing a tracheo-oesophageal fistula.

SUMMARY OF THE INVENTION

One aspect of the invention provides a tracheo-oesophageal fistula catheter as specified in claim 1.

A further aspect of the invention provides a method of sealing a tracheo-oesophageal fistula catheter as specified in claim 9.

Preferred aspects of the invention are specified in the claims dependent on claim 1.

The invention provides a catheter which is specifically designed for sealing a tracheo-oesophageal fistula. The catheter of the invention is more comfortable for patients to wear, and the seal provided is much more efficient than that achieved with existing apparatus. This improved seal leads to fewer infections, and may allow the patient to feed normally whilst the catheter is in place.

BRIEF DESCRIPTION OF THE DRAWINGS

In the drawings, which illustrate preferred embodiments of the invention by way of example.

DETAILED DESCRIPTION OF THE PREFERRED EMBODIMENTS

Figure 1:
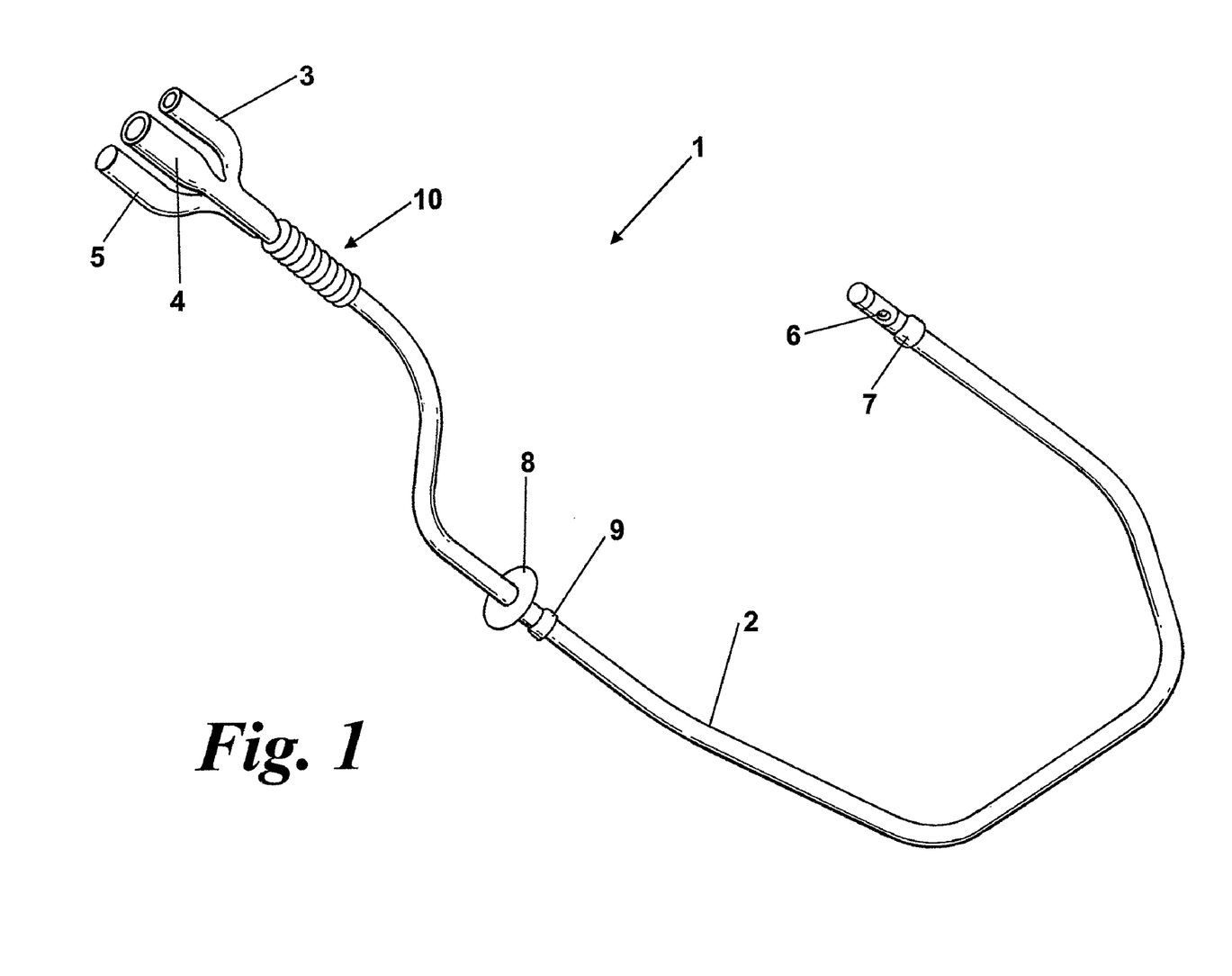
FIG. 1 shows a first embodiment of a tracheo-oesophageal fistula catheter with balloons in unexpanded form.
Figure 2:
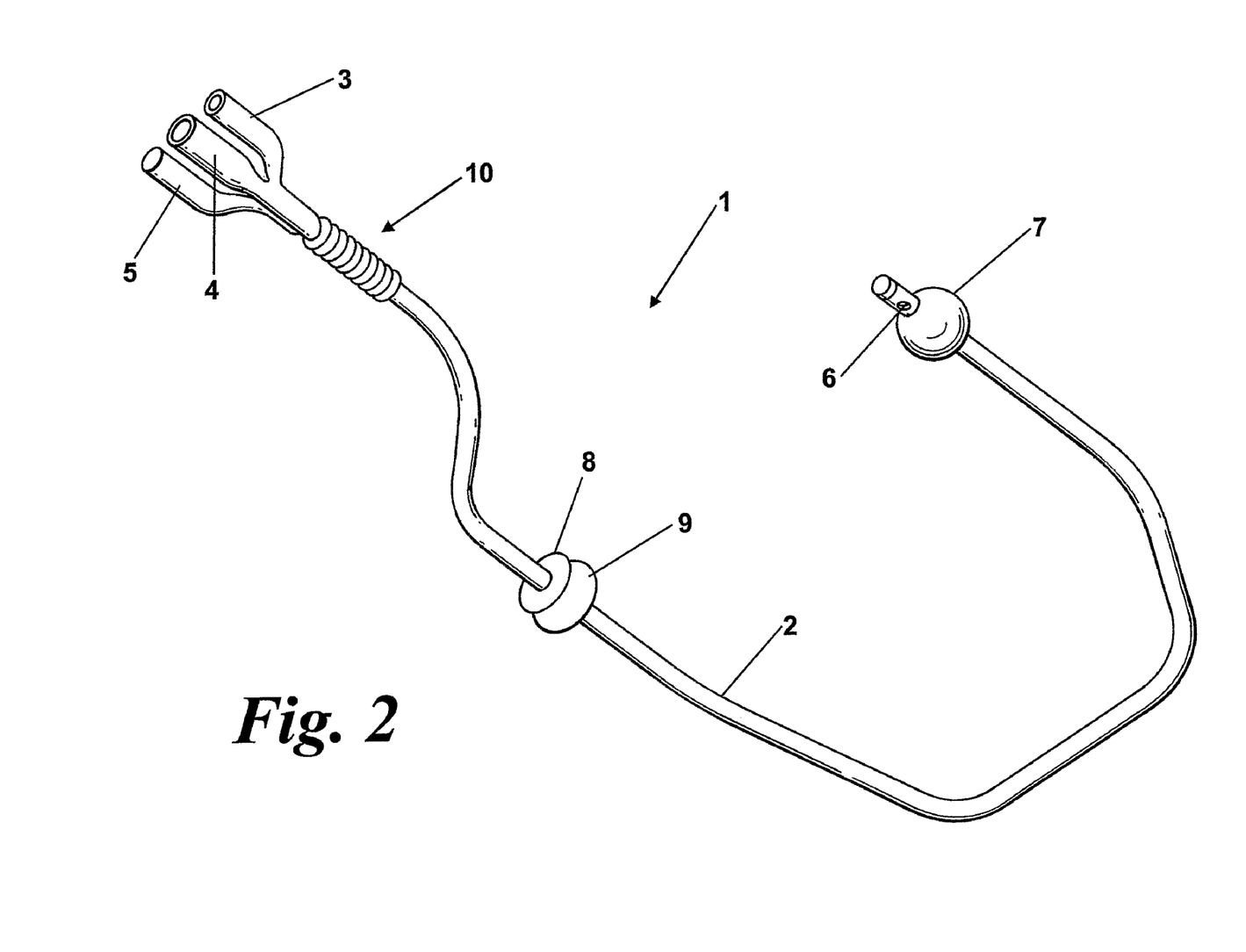
FIG. 2 shows the tracheo-oesophageal fistula catheter of FIG. 1 with balloons in expanded form.

With reference to FIGS. 1 and 2 a tracheo-oesophageal fistula catheter 1 comprises an elongate elongate conduit 2. At the top end of the conduit 2 there are three inlets 3, 4 and 5. At the bottom end of the conduit 2 there is an outlet 6. The outlet 6 is fluidly connected to one of the inlets 4 via a gastric lumen ($18^1$, $18^2$ or $18^3$, FIGS. 3a to c) within the conduit 2. In the context of this application, a lumen may be a channel within a conduit, or a discrete tube within a conduit. Adjacent to the outlet 6 at the bottom end of the conduit there is an expandable balloon 7 which is fluidly connected to one of the inlets 3 via a lumen ($17^1$, $17^2$ or $17^3$, FIGS. 3a to c) within the conduit 2. In FIG. 1 the balloon 7 is shown in unexpanded form, and in FIG. 2 in expanded form. The balloon 7 is expanded by injecting fluid through the inlet 3 via the lumen into the balloon 7. The inlet 3 includes a one-way valve to prevent fluid leaking out and to prevent the balloon 7 from deflating. The bottom end of the catheter is designed to be passed through a patient's tracheo-oesophageal fistula, down through the oesophagus and into the stomach with the balloon 7 in unexpanded form. Once the unexpanded balloon 7 is inside the stomach, the balloon 7 then expanded by introducing fluid into the outlet 3 which remains outside the body. The expanded balloon 7 prevents the bottom end of the catheter from leaving the stomach and secures the catheter in place.

Located on the outside of the conduit 2 is a flange 8 and an unexpanded balloon 9 separated by a short distance. The balloon 9 is fluidly connected with an inlet 5 via a lumen ($19^1$, $19^2$ or $19^3$, FIGS. 3a to c) within the conduit 2. In FIG. 1 the balloon 9 is shown in unexpanded form, and in FIG. 2 in expanded form. The flange 8 and the unexpanded balloon 9 are located on the conduit such that when the bottom end of the catheter has been inserted into a patient's oesophagus via the tracheo-oesophageal fistula, the said flange 8 and unexpanded balloon 9 are located on either side of the fistula. When these are in place, the balloon 9 is expanded by injecting fluid into the balloon 9 through the inlet 5. The inlet 5 includes a one-way valve to prevent fluid leaking out and to prevent the balloon from deflating. The inflated balloon 9 is forced against the front wall of the patient's oesophagus and pushes against the flange 8 providing a seal for the patient's fistula.

The balloon 9 may have a predetermined shape or may be inflated to a predetermined size. This would prevent over or under inflation of the balloon 9 and would reduce the risk of damage to surrounding tissues.

For comfort purposes the catheter conduit 2 may include a flexible portion at the top end of the catheter 1 such as a portion of concertina tubing 10. This allows the top end of the catheter 1 to be easily bent out of the way of the patient's face or tucked underneath clothing.

The patient may be fed through the catheter by introducing liquid into the inlet 4. The inlet 4 is fluidly connected with the outlet 6 via the gastric lumen ($18^1$ or $18^2$ or $18^3$, FIGS. 3a to c) within the conduit 2. When the catheter is in use the outlet 6 is inside the patient's stomach.

Alternatively the seal provided by the flange 8 and expanded balloon 9 may be sufficient to allow the patient to eat solid foods in the normal manner.

Figure 3A:
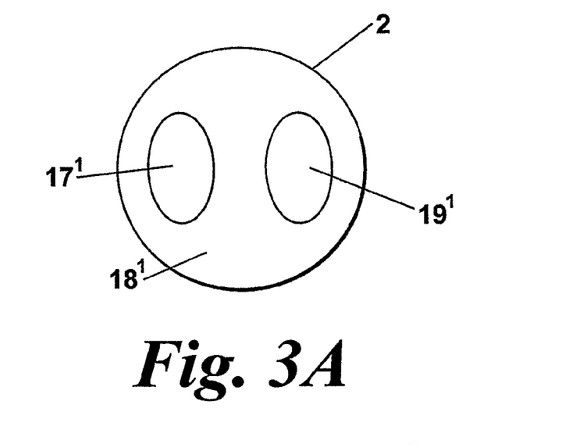
FIGS. 3a to c show three alternative cross-sectional views of the elongate conduit of tracheo-oesophageal fistula catheter of FIG. 1.

FIGS. 3a to c show various alternatives of the cross section of the conduit 2. In FIG. 3a the conduit 2 comprises three lumens $17^1$, $18^1$, and $19^1$. Lumens $17^1$ and $19^1$ are defined by two discrete tubes within the conduit 2. Lumens $17^1$ and $19^1$ are connected to balloons 7 and 9 and inlets 3 and 5 respectively. The gastric lumen $18^1$ is defined by the remaining interior space of the conduit 2.

Figure 3B:
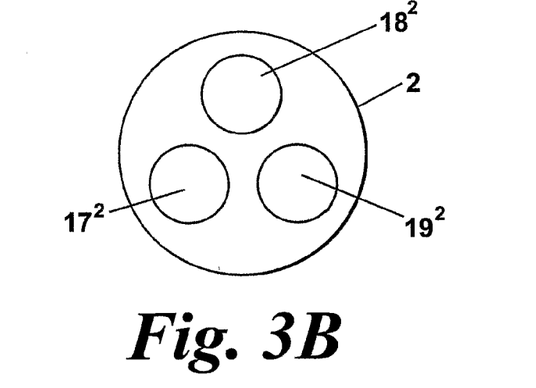

In an alternative embodiment shown in FIG. 3b, the conduit 2 comprises three lumens $17^2$, $18^2$, and $19^2$. Each lumen is defined by a discrete tube within the conduit 2. Lumens $17^2$ and $19^2$ are connected to balloons 7 and 9 and inlets 3 and 5 respectively. The gastric lumen $18^2$ is connected to inlet 4 and outlet 6. The conduit 2 acts as an outer sheath.

Figure 3C:
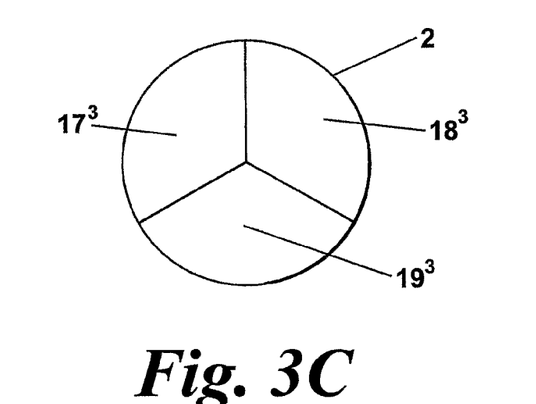

In an alternative embodiment shown in FIG. 3c, the conduit 2 is radially divided into three discrete channels. Lumens $17^3$, $18^3$, and $19^3$ are each defined by a separate channel. Lumens $17^3$ and $19^3$ are connected to balloons 7 and 9 and inlets 3 and 5 respectively. The gastric lumen $18^3$ is connected to inlet 4 and outlet 6.

Figure 4:
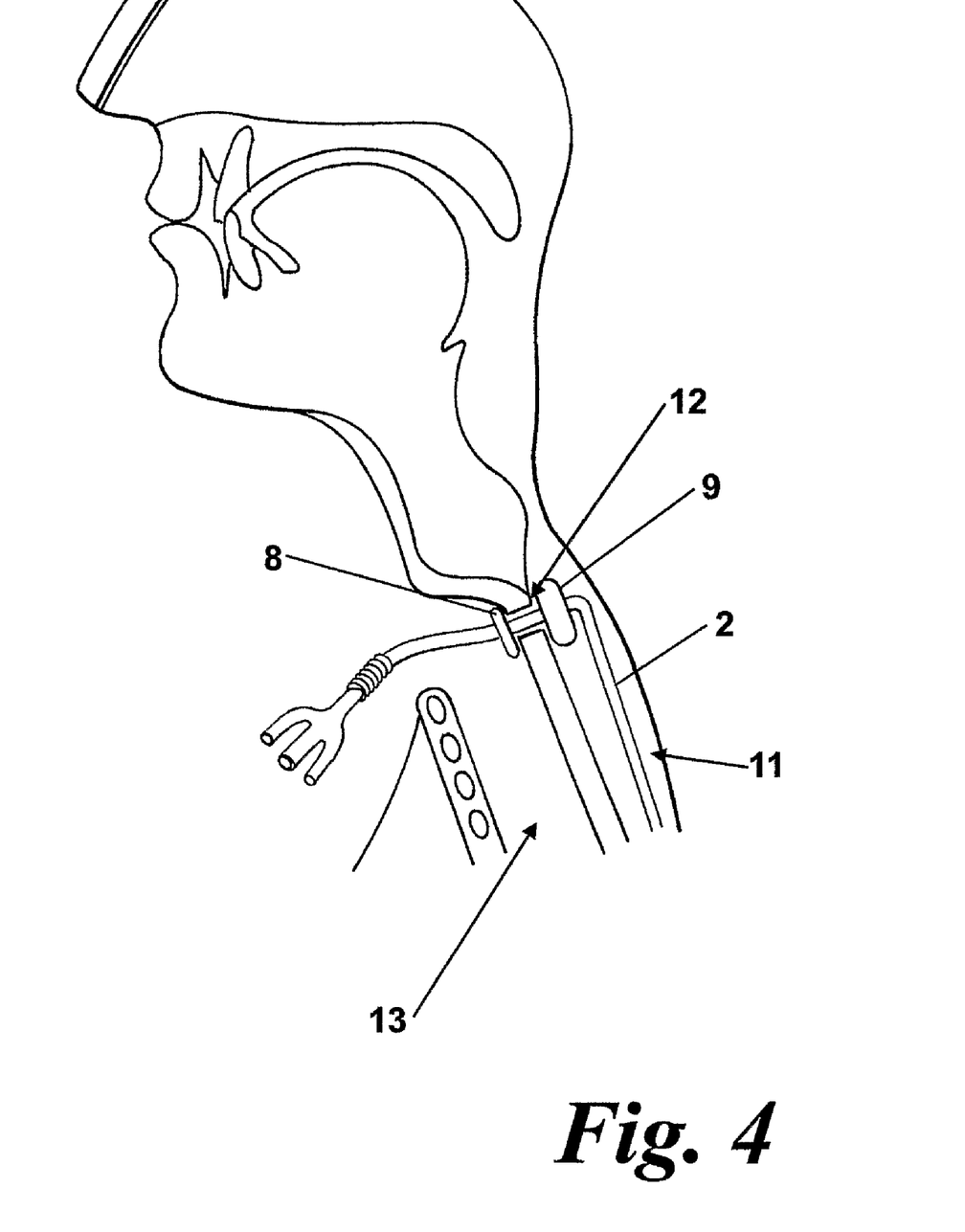
FIG. 4 shows a patient with the tracheo-oesophageal fistula catheter of FIG. 1 inserted into the oesophagus via the fistula.

FIG. 4 illustrates the top portion of the catheter in place in a patient's oesophagus 11. The tracheo-oesophageal fistula 12 is a hole between the oesophagus 11 and the trachea 13 which can be made following a laryngectomy operation. FIG. 4 illustrates the flange 8 and the expanded balloon 9 providing a seal for the fistula 12.

Figure 5:
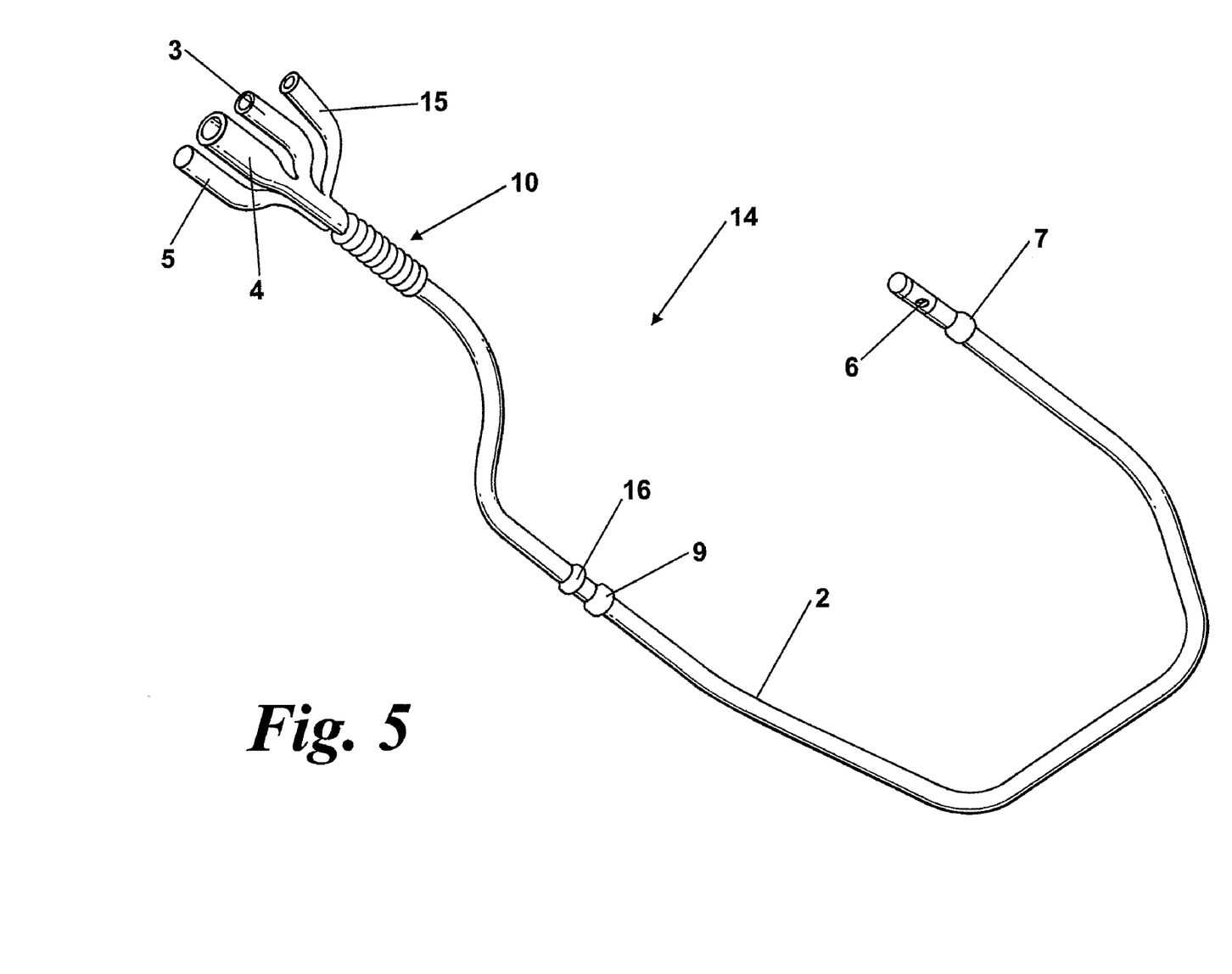
FIG. 5 shows an alternative embodiment of a tracheo-oesophageal fistula catheter with balloons in unexpanded form.
Figure 6:
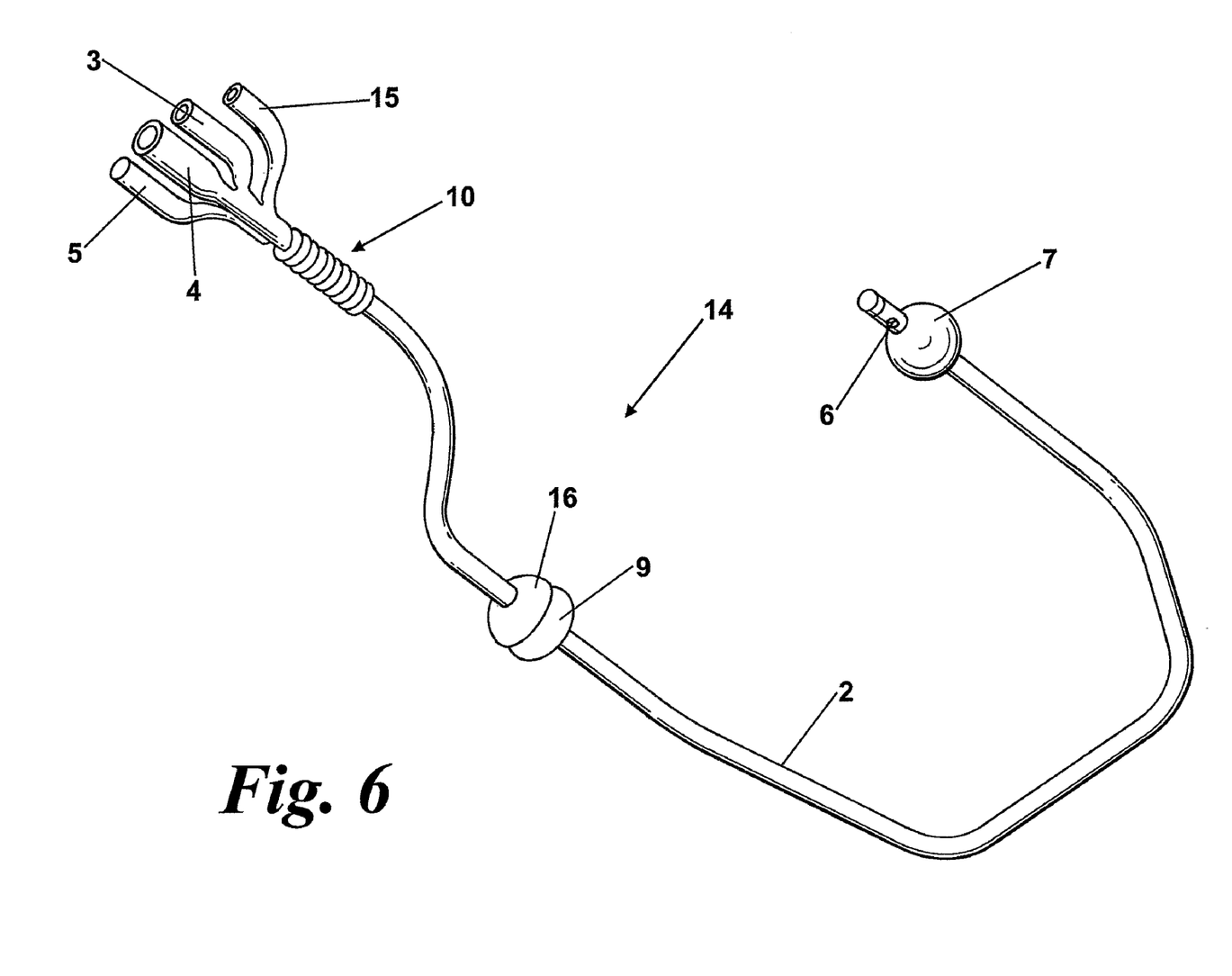
FIG. 6 shows the embodiment of FIG. 5 with balloons in expanded form.

An alternative embodiment of the invention is shown in FIGS. 5 and 6. Like features are referred to with like reference numerals.

With reference to FIGS. 5 and 6 an alternative embodiment of a tracheo-oesophageal fistula catheter 14 comprises an elongate conduit 2. At the top end of the conduit 2 there are four inlets 3, 4, 5 and 15. At the bottom end of the conduit 2 there is an outlet 6. The outlet 6 is fluidly connected to one of the inlets 4 via a gastric lumen ($20^1$, $20^2$ or $20^3$, FIGS. 7a to c) within the conduit 2. Adjacent to the outlet 6 at the bottom end of the conduit there is an expandable balloon 7 which is fluidly connected to one of the inlets 3 via a lumen ($22^1$, $22^2$ or $22^3$, FIGS. 7a to c) within the conduit 2. In FIG. 4 the balloon 7 is shown in unexpanded form, and in FIG. 5 in expanded form. The balloon 7 is expanded by injecting fluid through the inlet 3 via the lumen into the balloon 7. The inlet 3 includes a one-way valve to prevent fluid leaking out and to prevent the balloon from deflating. The bottom end of the catheter is designed to be passed through a patient's tracheo-oesophageal fistula, down through the oesophagus and into the stomach with the balloon 7 in unexpanded form. Once the unexpanded balloon 7 is inside the stomach, the balloon 7 is expanded by introducing fluid into the outlet 3 which remains outside the body. The expanded balloon 7 prevents the bottom end of the catheter from leaving the stomach and secures the catheter in place.

Located on the outside of the conduit 2 is a pair of unexpanded balloons 9 and 16 separated by a short distance. The first balloon 16 is fluidly connected with an inlet 15 via a lumen ($21^1$, $21^2$ or $21^3$, FIGS. 7a to c) within the conduit 2, and the second balloon 9 is fluidly connected with an inlet 5 via a similar lumen within the conduit 2. In FIG. 5 the balloons 9 and 16 are shown in unexpanded form, and in FIG. 6 in expanded form. The unexpanded balloons 9 and 16 are located on the conduit such that when the bottom end of the catheter has been inserted into a patient's oesophagus via the tracheo-oesophageal fistula, the said unexpanded balloons are located on either side of the fistula. When in place, each balloon is expanded by injecting fluid into each respective inlet 5 or 15. The inlets each include a one-way valve to prevent fluid leaking out and to prevent the balloons from deflating. The inflated balloons 9 and 16 are forced together on either side of the fistula, providing a seal for the patient's fistula.

Figure 7A:
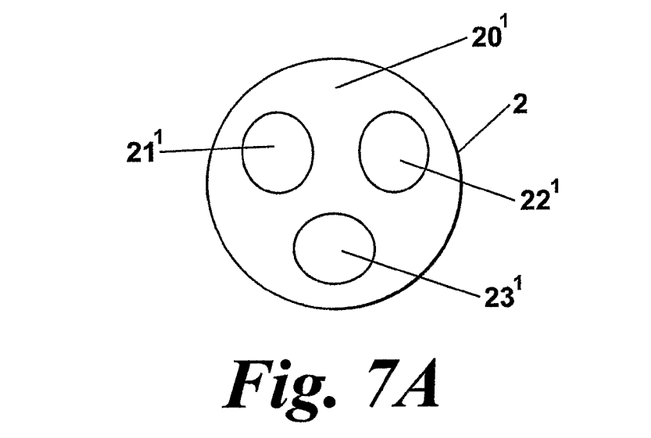
FIGS. 7a to c show three alternative cross-sectional views of the elongate conduit of tracheo-oesophageal fistula catheter of FIG. 5.

FIGS. 7a to c show various alternatives of the cross section of the conduit 2. In FIG. 7a the conduit 2 comprises four lumens $20^1$, $21^1$, $22^1$ and $23^1$. Lumens $21^1$, $22^1$, and $23^1$ are defined by three discrete tubes within the conduit 2. Lumens $21^1$, $22^1$, and $23^1$ are connected to balloons 16, 9 and 7 and inlets 15, 5, and 3 respectively. The gastric lumen $20^1$ is defined by the remaining interior space of the conduit 2.

Figure 7B:
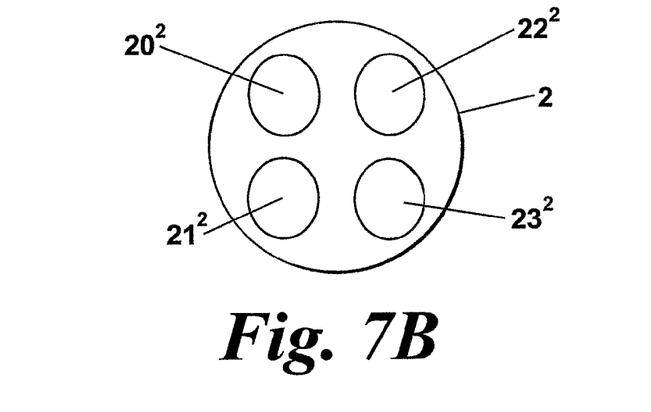

In an alternative embodiment shown in FIG. 7b, the conduit 2 comprises four lumens $20^2$, $21^2$, $22^2$ and $23^2$. Each lumen is defined by a discrete tube within the conduit 2. Lumens $21^2$, $22^2$, and $23^2$ are connected to balloons 16, 9 and 7 and inlets 15, 5, and 3 respectively. The gastric lumen $20^2$ is connected to inlet 4 and outlet 6. The conduit 2 acts as an outer sheath.

Figure 7C:
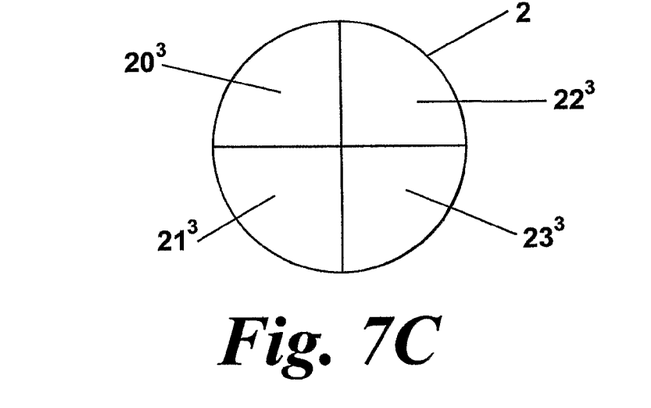

In an alternative embodiment shown in FIG. 7c, the conduit 2 is radially divided into four discrete channels. Lumens $20^3$, $21^3$, $22^3$ and $23^3$ are each defined by a separate channel. Lumens $21^3$, $22^3$, and $23^3$ are connected to balloons 16, 9 and 7 and inlets 15, 5, and 3 respectively. The gastric lumen 203 is connected to inlet 4 and outlet 6.

As with the first embodiment, the catheter conduit 2 may include a flexible portion at the top end of the catheter 1 such as a portion of concertina tubing 10. This allows the top end of the catheter 14 to be easily bent out of the way of the patient's face or tucked underneath clothing.

As with the first embodiment, the patient may be fed through the catheter 14 by introducing liquid into the inlet 4. The inlet 4 is fluidly connected with the outlet 6 via a lumen ($20^1$, $20^2$ or $20^3$, FIGS. 7a to c) within the conduit 2. When the catheter is in use the outlet 6 is inside the patient's stomach.

Alternatively the seal provided by the expanded balloons 9 and 16 may be sufficient to allow the patient to eat solid foods in the normal manner.

The invention claimed is:

1. A tracheo-oesophageal fistula catheter comprising:
   (a) an elongate conduit having a proximal and a distal end, the conduit comprising a plurality of lumens commencing adjacent to the proximal end;
   (b) means for substantially sealing a tracheo-oesophageal fistula, the means being attached to the conduit adjacent to the proximal end and comprising two elements to be placed on either side of the fistula; and
   (c) at least one expandable balloon attached to the conduit adjacent to the distal end, and in fluid connection with at least one of said lumens;
   wherein at least one lumen is a gastric lumen, the gastric lumen extending along the full length of the conduit and having an outlet at the distal end of the conduit, and wherein at least one element of the means for sealing the fistula comprises an expandable balloon in fluid connection with at least one of said lumens.

2. A tracheo-oesophageal fistula catheter as claimed in claim 1, wherein one element of the means for sealing the fistula comprises a flange.

3. A tracheo-oesophageal fistula catheter as claimed in claim 1, wherein each element of the means for sealing the fistula comprises an expandable balloon, each in fluid connection with at least one of said lumens.

4. A tracheo-oesophageal fistula catheter as claimed in any preceding claim, wherein each of said lumens has an inlet at the proximal end of the conduit.

5. A tracheo-oesophageal fistula catheter as claimed in claim 4, wherein each expandable balloon is expanded by introducing fluid into the lumen fluidly connected with said balloon via said inlet.

6. A tracheo-oesophageal fistula catheter as claimed in claim 4 or 5, wherein the inlet of each lumen except the at least one gastric lumen comprises a one-way valve.

7. A tracheo-oesophageal fistula catheter as claimed in any preceding claim, wherein the proximal end of the conduit includes a flexible element.

8. A tracheo-oesophageal fistula catheter as claimed in claim 7, wherein the flexible element comprises concertina tubing.

9. A method of sealing a tracheo-oesophageal fistula using the catheter as described in any of claims 1 to 8, the method comprising the steps of:
   (a) inserting the catheter into the oesophagus through a patient's tracheo-oesophageal fistula with each expandable balloon in unexpanded form;
   (b) inserting the distal end of the catheter into the patient's stomach such that the unexpanded balloon adjacent to the distal end of the conduit passes into the stomach;
   (c) positioning each element of the means for sealing the fistula on either side of the fistula;
   (d) expanding the at least one balloon attached adjacent to the distal end of the catheter by introducing fluid into the lumen fluidly connected with said balloon;
   (e) expanding the at least one balloon attached adjacent to the proximal end of the catheter by introducing fluid into the lumen fluidly connected with said balloon.

* * * * *